United States Patent [19]

Ishikawa et al.

[11] Patent Number: 4,578,503

[45] Date of Patent: Mar. 25, 1986

[54] ALKYLATED OR ALKENYLATED MALONIC ACID OR ITS DERIVATIVES HAVING A FLUORINE

[75] Inventors: Nobuo Ishikawa; Takeshi Nakai, both of Yokohama; Yoshio Inouye, Machida, all of Japan

[73] Assignee: Daikin Kogyo Co., Ltd., Osaka, Japan

[21] Appl. No.: 528,134

[22] Filed: Aug. 31, 1983

[30] Foreign Application Priority Data

Aug. 31, 1982 [JP] Japan ............................. 57-151007
Aug. 31, 1982 [JP] Japan ............................. 57-151008

[51] Int. Cl.$^4$ ................ C07C 67/317; C07C 69/612; C07C 57/36
[52] U.S. Cl. ................................. 560/82; 560/176; 560/192; 562/459; 562/489; 562/578; 562/596
[58] Field of Search ................ 560/82, 176, 192; 562/459, 489, 578, 596

[56] References Cited

U.S. PATENT DOCUMENTS 3,478,116 11/1969 Smeltz ............................. 560/192 X

FOREIGN PATENT DOCUMENTS 38735 10/1981 European Pat. Off.
57-85338 5/1982 Japan .

OTHER PUBLICATIONS

Stubbe et al., The Journal of Biological Chemistry, vol. 255, No. 1, Jan. 10, 1980, pp. 236–242.

Primary Examiner—Natalie Trousof
Assistant Examiner—Vera C. Clarke
Attorney, Agent, or Firm—Armstrong, Nikaido, Marmelstein & Kubovcik

[57] ABSTRACT

An alkylated or alkenylated malonic ester having a fluorine containing aliphatic substituent and derivatives thereof as expressed by the following general formula:

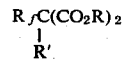

where $R_f$ is a fluorine containing aliphatic group, R is an aliphatic group, or hydrogen or alkali metal atom, and R' is an unsubstituted or substituted aliphatic group.

And a method to trap the enolate ion of a malonic ester having a fluorine containing aliphatic substituent as expressed by the following general formula,

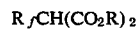

where $R_f$ is a fluorine containing aliphatic group, and R is an aliphatic group, hydrogen or alkali metal atom, wherein said malonic ester is converted under the action of a weaker base and/or fluoride ion to a fluorine containing enolate ion to be trapped as expressed by the following general formula:

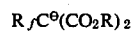

where $R_f$ and R are the same as above.

9 Claims, No Drawings

ALKYLATED OR ALKENYLATED MALONIC ACID OR ITS DERIVATIVES HAVING A FLUORINE

BACKGROUND OF THE INVENTION

1. Field of the Invention

This invention relates to a new and useful alkylated or alkenylated malonic acid or its derivatives having a fluorine containing aliphatic substituent and a method to trap the enolate ion of the malonic acid or its derivatives.

2. Description of the Prior Art

There are known some compounds which, having a fluorine containing aliphatic group, for example, trifluoromethyl group, exhibit biological activities. As one of the methods of synthesis of such $CF_3$ containing compound, there is a reaction that gives rise to various carbon-carbon bonds on a building block having a $CF_3$ group. Success in such method depends on how a building block having a $CF_3$ group can be synthesized or produced.

OBJECTS AND SUMMARY OF THE INVENTION

An object of the present invention is to provide a new and useful alkylated or alkenylated malonic acid or its derivatives having a fluorine containing aliphatic substituent.

Another object of the invention is to provide an effective means to produce the above compound, that is, a new and useful method to trap the enolate ion of a malonic acid or its derivatives having a fluorine containing aliphatic substituent, for example, the above α-trifluoromethylmalonic ester, without elimination of any fluoride ion.

Namely, the first aspect of the invention is an alkylated or alkenylated malonic acid or its derivatives having a fluorine containing aliphatic substituent and its derivatives as expressed by the following general formula:

where $R_f$ is a fluorine containing aliphatic group, R is an aliphatic group, or hydrogen or alkali metal atom and R' is a substituted or unsubstituted aliphatic group.

The above ester or its derivatives embodying the invention, which are endowed with the superior properties that a fluoro compound exhibits because of the presence of a fluorine atom or atoms in its molecule, may be used as a starting material for the synthesis of various useful substances, for example, trifluoromethylated aliphatic or heterocyclic compounds.

In this first aspect, $R_f$ in the above general formula preferably has up to 5 carbon atoms. Examples of such $R_f$ are fluoromethyl, fluoroethyl, and fluoropropyl groups. Further, R and R' may be alkyl groups having up to 5 carbon atoms each, for example, methyl, ethyl, and propyl groups, or alkenyl groups also having up to 5 carbon atoms each though they may have an aryl substituent in their chain regardless of whether they are alkyl or alkenyl.

The second aspect of the invention is a method to trap the enolate ion of a malonic acid or its derivative having a fluorine containing aliphatic substituent as expressed by the following general formula, $$R_fCH(CO_2R)_2$$

where $R_f$ is a fluorine containing aliphatic group and R is an aliphatic group, hydrogen or alkali metal atom, wherein the above malonic acid or its derivative is converted by action of a weaker base and/or fluoride ion to a fluorine containing enolate ion to be trapped as expressed by the following general formula:

$$R_fC^{\ominus}(CO_2R)_2$$

where $R_f$ and R are the same as above.

In this method, because of the use of a weaker base as mentioned above, the malonic ester having a fluorine containing aliphatic substituent, for example, α-trifluoromethylmalonic ester, is not fully stripped of the hydrogen atom at its α-position and therefore no fluoride ion ($F^{\ominus}$) is eliminated from its molecule, thus allowing the enolate ion to be trapped. Also when a fluoride ion is used for the base, the enolate ion can be trapped since the equilibrium between the above enolate ion and alkenylmalonic acid or its derivative that is formed as such enolate ion is further defluorinated is shifted toward the former under the presence of additional fluoride ion.

Based on the second discovery, the reaction can be stopped at the stage of the enolate ion, or the ion trapped, which can be reacted with various reactive substances, for example, to form its Michael adduct, alkylated product, etc. These products and also enolate ion itself find wide applications in the organic synthesis. For example, they can be used as a starting material for fluorine containing compounds such as trifluoromethylated aliphatic or heterocyclic compounds.

In the method of the second aspect the base used is preferably trialkylamine whose alkyl groups have up to 5 carbon atoms or cesium fluoride. Examples of such alkyl groups are methyl, ethyl and propyl groups. Beside, the $R_f$ of the above malonic acid or its derivative having a fluorine containing aliphatic substituent preferably has up to 5 carbon atoms. Preferable examples of such $R_f$ are fluoromethyl, fluoroethyl and fluoropropyl groups. The R of the same ester has up to 5 carbon atoms, examples of which are methyl, ethyl and propyl groups.

DESCRIPTION OF THE PREFERRED EMBODIMENTS

The invention has been conceived of as described below. As shown in the following reaction formula, for example, trifluoromethylmalonic ester 1 that has a highly acidic α-hydrogen atom can be converted to its enolate ion 2 under the action of a base.

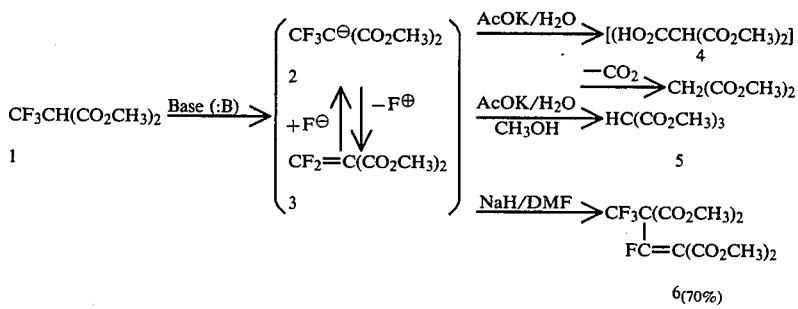

It was found, however, that the generated enolate ion 2 readily releases a fluoride ion from its $CF_3$ group resulting in difluoromethylenemalonic ester 3, which immediately undergoes a reaction with a nucleophilic substance to fully lose the original $CF_3$ group by repeating the fluoride ion separation. For example, in aqueous potassium acetate solution, the enolate ion 2 is converted through the carboxylic acid 4 to malonic ester while, in methanolic aqueous potassium acetate solution, it is converted to triester 5. And when a base/solvent system sodium hydride/dimethylformamide (DMF) that exhibits no nucleophilic behavior is used, the Michael addition of the enolate ion 2 to the compound 3 followed by fluoride ion separation results in a condensation product 6.

It was confirmed, however, by $^{19}F$ NMR spectroscopy that if trialkylamine, for example, triethylamine is used for the base the above reaction does not proceed from 1 to 3 but stops at the stage of the enolate ion 2. This probably occurs because with triethylamine that is a weak base the ester 1 is not fully stripped of the α-hydrogen atom, namely, there is no full removal of HF therefrom. Using a base/solvent system based on the above in which the fluoride ion elimination is avoided, therefore, it is expected the enolate ion 2 may be successfully trapped.

With vinyl ketones that work well as electrophilic reagents, corresponding Michael adducts 7 could be produced according to the following reaction formula. These adducts can be converted to corresponding ketones by decarboxylation.

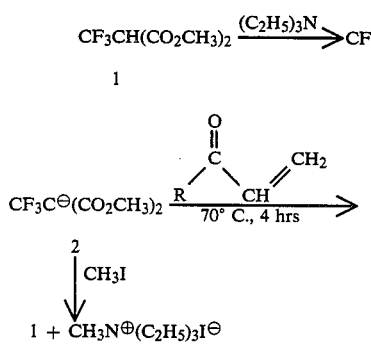

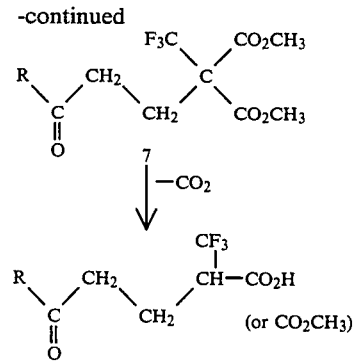

Table 1 shows Michael adducts 7 thus prepared.

TABLE 1

| R | Yield (%) | bp (°C./mmHg) |
|---|---|---|
| $CH_3$ | 74 | 88~89/0.2 |
| $C_2H_3$ | 66 | 89~91/0.2 |

It is noted, however, that even if the enolate ion 2 is reacted with methyl iodide, no methylation occurs on the $C^\ominus$ position of 2 but priority is given to the reaction to form the quaternary amine with the enolate ion 2 being converted to the starting material malonic ester 1.

To alkylate malonic ester 1 with alkyl halide, the present inventors thus tried to carry out the following reaction:

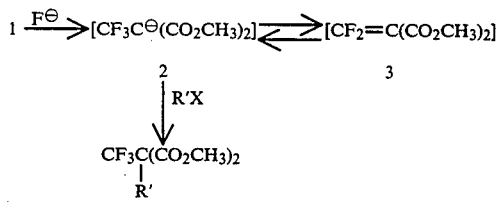

Namely, using an excess of fluoride ion $F^\ominus$ as base, the equilibrium between 2 and 3 was shifted toward 2 to carry out a reaction with alkyl halide (R'X).

For the fluoride ion source, 3 equiv. of cesium fluoride was used. Table 2 summarizes the results.

TABLE 2

| R'X | Method | Yield of 8 (%) | bp (°C./mmHg) |
|---|---|---|---|
| $CH_3I$ | A* | 60 | 6.3~65/10 |
| $PhCH_2Br$ | B** | 45 | 91~94/0.3 |
| $CH_2=CHCH_2Br$ | B** | 47 | 90~94/9 |

*Method A: R'X-1.1 equiv., room temp., 12 hr
**Method B: R'X-2.5 equiv., 70–75° C, 2 hr The by-product of the above reaction is the aforementioned condensation product 6. Namely, with an alkyl halide of low reactivity, little alkylated compound 8 is produced but only the condensation product 6 is obtained. By contrast, using alkyl halides in Table 2, halogenated products 8 embodying the invention could be produced at comparatively high yield. These halogenated products were identified by NMR spectroscopy with the following structural formulas:

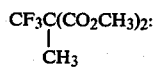

NMR ($^{19}$F shifts from ext. CF$_3$CO$_2$H) F: Chemical shift with CF$_3$ −7.5 (s). H: COCH$_3$: 3.81 (s), R (=CH$_3$): 1.66 (s).
IR 1750 cm$^{-1}$ (C=O)
Elementary analysis: C: 39.40. H: 4.21.

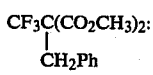

NMR F: −12.2 (s). H: CO$_2$CH$_3$: 3.73 (s), CH$_2$: 3.50 (s), Ph: 7.29 (s).
IR 1745 cm$^{-1}$ (C=O).
Elementary analysis: C: 53.58. H: 4.49.

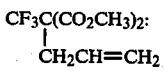

NMR F: −10.6 (s). H: CO$_2$CH$_3$: 3.79 (s), CH$_2$: 2.85 (d).
IR 1755 cm$^{-1}$ (C=O)
Elementary analysis: C: 45.19. H: 4.54.

Further, when an attempt was made to synthesize an enolate ion equivalent, or silyl ketene acetal 9 according to the following formula by a (C$_2$H$_5$)$_3$N/(CH$_3$)$_3$SiCl system, only the condensation product 6 was produced without any formation of the expected ketene acetal.

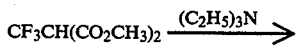

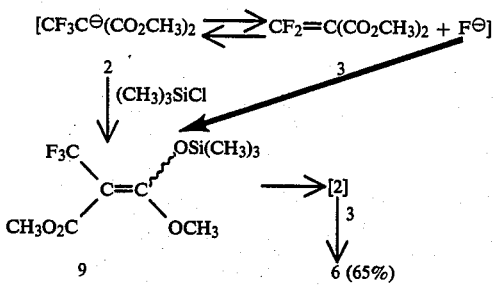

The explanation of why there was attained the same result as with the already mentioned base/solvent system making use of sodium hydride, namely, the production of the condensation product 6, is that the fluoride ion that is present in a trace in the reaction system attacks silyl ketene acetal as it is formed to produce the stripped enolate ion 2.

It is noted that the starting material 1 in the above reaction can be synthesized by the following method.

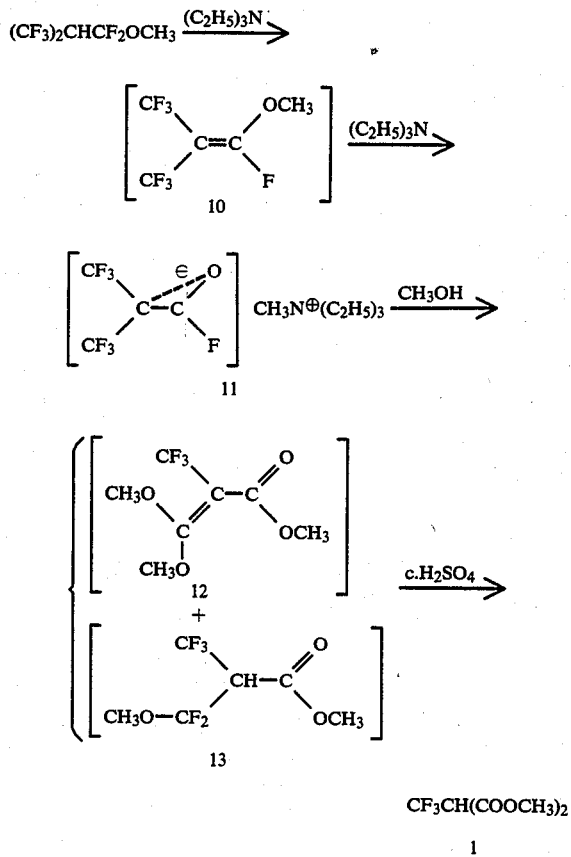

This reaction can be conducted, for example, under the following condition. First, an octafluoroisobutene-methanol adduct is reacted with 2 equiv. of triethylamine in an aprotic polar solvent, such as dimethylformamide to form a quarternary-ammonium enolate 11 through heptafluoroisobutylmethylether 10 in situ, namely, without removal of solvent. Next methanol is slowly added dropwise to the reaction mixture in an ice bath. Agitation, for example, for an hour after the methanol addition produces a ketene acetal 12 with a small amount of a monoester 13. Further agitation for more hours in methanol converts the above ketene acetal to an orthoester. If the reaction mixture at this stage is poured into water and the oily layer is separated and treated with conc. sulfuric acid, the ketene acetal 12 and monoester 13 are simultaneously hydrolyzed to convert to the intended product dimethyl trifluoromethylmalonate 1 at a high yield.

It is noted that in the above reaction an aprotic polar solvent is used to react the quarternary ammonium enolate with alcohol and that this alcohol is added not at once but slowly over a period of time and particularly dropwise. The intermediate product to be reconverted to the intended malonic ester can thus be produced abundantly enough to improve the yield of the intended product substantially.

The above embodiments are set forth as a further description but are not to be construed as limiting the invention thereto. Modifications and variations are possible without departing from the spirit and scope of the invention.

For example, in the compound 1, the trifluoromethyl group can be replaced with another fluorohydrocarbon group and the methyl group with another aliphatic hydrocarbon group while the CO₂R group can be hydrolized to COOH or reacted with an alkali hydroxide for conversion to an alkali salt, for example, sodium salt. Further, in the above process to produce 8, other alkyl halides can be used for R'X to obtain the corresponding alkylated compounds. In addition, the compound 8 can be hydrolized or treated with alkali hydroxide to give a corresponding acid or alkali salt.

The invention will be understood more clearly with reference to the following examples:

EXAMPLE 1

A mixture of dried CsF (9.11 g, 60 mmol), diglyme (41 ml), dimethyl(trifluoromethyl)malonate (4 g, 20 mmol), and methyl iodide (3.12 g, 22 mmol) was stirred overnight at room temperature. The reaction mixture was poured into water and the resultant oily layer and the ether-extract from the aqueous layer were combined and washed with water to remove diglyme. After drying over MgSO₄, the ether was evaporated and the residue was subjected to distillation, giving dimethyl methyl(trifluoromethyl)malonate (2.56 g, 60%), b.p. 63°-65° C./10 mmHg. This product showed the following analytical properties: ¹⁹F NMR: δ—7.5 (s, C$\underline{F}_3$); ¹H NMR: δ 3.81 (s, 6H, CO₂C$\underline{H}_3$), 1.66 (s, C$\underline{H}_3$).

EXAMPLE 2

Into a mixture of dried and powdered CsF (9.11 g, 60 mmol), benzyl bromide (8.55 g, 50 mmol), and diglyme (16 ml), a solution of dimethyl(trifluoromethyl)malonate (4.0 g) in diglyme (20 ml) was added at 70°-75° C. over a period of 70 min. After being stirred for 50 min at that temperature, the reaction mixture was poured into water and worked up as usual. Benzyl(trifluoromethyl)malonate (2.6 g, 45%) was distilled out at 91°-94° C./0.3 mmHg.

EXAMPLE 3

Into a mixture of sodium hydride (0.36 g, 15 mmol) and N,N-dimethylformamide (5 ml), a solution of dimethyl(trifluoromethyl)malonate (2.00 g, 10 mmol) in N,N-dimethylformamide (5 ml) was added dropwise with cooling the vessel in an ice-bath. After being stirred for 2 h at room temperature, the reaction mixture was poured into dilute aqueous HCl, and worked up as usual. Distillation under vacuum gave tetramethyl 2,4,4,4-tetrafluoro-1-butene-1,1,3,3-tetra-carboxylate (1.27 g, 70%), b.p. 122°-124° C./0.3 mmHg. Found: C: 40.74; H: 3.53%. Calcd.for C₈H₁₂O₈F₄: C: 40.01; H: 3.36%. ¹⁹F NMR: δ—15.1 (d. C$\underline{F}_3$), +10.7 (q, =C$\underline{F}$—). ¹H NMR: δ 3.77 (s, C$\underline{H}_3$), 3.$\overline{87}$ (s, C$\underline{H}_3$), 3.90 (COC$\underline{H}_3$)). IR: 1665 (C=C), 17$\overline{50}$ (C=O) cm$^{-1}$

EXAMPLE 4

Into a methanolic solution of sodium methoxide prepared from sodium (0.46 g, 20 mmol) and dried methanol (10 ml), a solution of dimethyl(trifluoromethyl)malonate (0.87 g) in methanol (4 ml) was added.

After 3.5 h of stirring at room temperature, the reaction mixture was poured into dil. aqueous HCl and worked up as usual. Removal of the ether gave pure dimethyl methyl-malonate (0.39 g, 67%) which was identified by comparing its IR, ¹H NMR, and GLC data with those of an authentic sample.

EXAMPLE 5

A mixture of dimethyl(trifluoromethyl)malonate (4.0 g, 20 mmol), methyl vinyl ketone (1.54 g, 22 mmol), triethylamine (0.30 g, 3 mmol), and pyridine (20 ml) was heated for 4 h at 70° C. The reaction mixture was poured into water and worked up as usual. The adduct, dimethyl 1,1,1-trifluoro-5-oxo-2,2-hexanedicarboxylate (3.97 g), b.p. 88°-89° C./0.2 mmHg, was obtained and identified in a similar way.

What is claimed is:

1. An alkylated or alkenlated malonic acid or its acid salts and esters having a fluorine containing aliphatic substitutent, as expressed by the following formula:

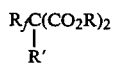

where $R_f$ is a fluorine containing aliphatic group, R is an aliphatic group, or hydrogen or alkali metal atom, and R' is an aryl substituted aliphatic group.

2. An acid or its acid salts and esters as claimed in claim 1 wherein said $R_f$ has 5 carbon atoms at most.

3. An acid or its acid salts and esters as claimed in any one of claims 1 or 2, wherein said aliphatic group of said R' is an alkyl or alkenyl group having 5 carbon atoms at most.

4. A method to trap the enolate ion of a malonic acid or its acid salts and esters having a fluorine containing aliphatic substitutent, as expressed by the following formula,

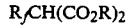

where $R_f$ is a fluorine containing aliphatic group and R is an aliphatic group, hydrogen or alkali metal atom, wherein said malonic acid or its acid salts and esters is converted under the action of a weaker base or fluoride ion to a fluorine containing enolate ion to be trapped as expressed by the following formula:

where $R_f$ and R are the same as above.

5. A method as claimed in claim 4 wherein said weaker base is trialkylamine.

6. A method as claimed in claim 5 wherein each alkyl group of said trialkylamine has 5 carbon atoms at most.

7. A method as claimed in one of claims 4 to 6 wherein cesium fluoride is used for the source of said fluoride ion.

8. A method as claimed in any one of claims 4 to 6 wherein said $R_f$ has 5 carbon atoms at most.

9. A method as claimed in any one of claims 4 to 6 wherein said R has 5 carbon atoms at most.

* * * * *